United States Patent [19]

Kim et al.

[11] Patent Number: 4,478,830

[45] Date of Patent: Oct. 23, 1984

[54] GLYCOSYLATED INSULIN DERIVATIVES

[76] Inventors: Wan S. Kim, 4512 Jupiter Dr., Salt Lake City, Utah 84117; Seo Y. Jeong, 716 Medical Place N., Salt Lake City, Utah 84112; James C. McRea, 1876 East 2700 S., Salt Lake City, Utah 84106

[21] Appl. No.: 532,917

[22] Filed: Feb. 6, 1984

Related U.S. Application Data

[62] Division of Ser. No. 442,362, Nov. 17, 1982, Pat. No. 4,444,683.

[51] Int. Cl.$^3$ .............................................. A61K 37/26
[52] U.S. Cl. .................................................... 424/178
[58] Field of Search ..................... 424/178; 260/112.7

[56] References Cited

U.S. PATENT DOCUMENTS 3,591,574 7/1971 Fenichel et al. .................... 424/178

Primary Examiner—Frederick E. Waddell
Attorney, Agent, or Firm—Thorpe, North & Western

[57] ABSTRACT

Synthesized succinyl and glutaryl glucosamines, p-(succinylamido)-phenyl-α-D-gluco- and mannopyranosides, p-(glutarylamido)-phenyl-α-D-gluco- and mannopyranosides and p-(isothiocyanotophenyl)-α-D-gluco- and mannopyranosides are reacted with insulin to form corresponding glycosylated insulins containing from 1 to 3 glycosyl groups per insulin molecule. The novel glycosylated insulins resist aggregation and show significant activity in depressing blood sugar levels.

4 Claims, 4 Drawing Figures

GLYCOSYLATED INSULIN DERIVATIVES

This application is a division of application Ser. No. 442,362, filed Nov. 17, 1982, now U.S. Pat. No. 4,444,683.

BACKGROUND OF THE INVENTION

This invention relates to the preparation of glycosylated insulins. More particularly, this invention relates to the preparation of glycosylated insulins and to novel intermediates to be used in preparing glycosylated insulins.

Various systems have been proposed for the delivery of insulin to a diabetic patient that will be more responsive to the needs of the patient.

The bioengineering approach is directed towards design of insulin infusion pumps. Hundreds of diabetics presently used external battery-operated pumps. The pump injects insulin continuously through a needle attached to a catheter inserted into a vein or into subcutaneous tissue. The flow can be adjusted manually when a change occurs in the amount of insulin needed. The units are usually worn on a belt or strapped to a leg.

Still in an experimental stage are pumps that deliver an amount of insulin precisely determined by a sensor that measures blood glucose levels. Though successful progress has been made in this area, these pumps are still too heavy to be portable. Another difficulty is that the system needs an apparatus for the continuous sampling of blood, an analyzer to determine the blood glucose level rapidly and continuously, a computer to analyze the results and to determine the appropriate insulin dose, and an infusion pump to deliver insulin intravenously in a manner approximating the delivery by the beta cells of the pancreas. Efforts are underway to reduce the size of the system and prolong its sensor's life. A "vest pocket" model, a system the size of a cigarette pack containing glucose sensor, power source, computer, insulin reservoir and pump, has been reported by Elliot in *J. Am. Med. Assoc.*, 241, 223 (1979).

Another obstacle at present is the lack of an accurate implantable electrode to sense the concentration of blood glucose. Again, a through-the-skin connection to the patient's blood stream for long periods presents risks of infection and clotting problems. Also, the occurring aggregation of insulin in the artificial delivery systems poses a considerable problem since the aggregated insulin will precipitate or crystallize out of solution, thereby reducing the bioavailability of the insulin in an insulin reservoir. In addition, the aggregated insulin can become lodged in the delivery needle and prevent the flow of insulin from the delivery system to the diabetic.

OBJECTS AND SUMMARY OF THE INVENTION

It is, therefore, an object of the present invention to prepare a semisynthetic insulin which will not aggregate as rapidly as native insulin and, therefore, have a longer storage life.

It is also an object of the present invention to prepare novel intermediate compounds to be used in the preparation of non-aggregating semisynthetic insulins.

A still further object of the present invention is to prepare glycosylated insulins which possess significant biological activity in depressing blood sugar levels.

These and other objects may be accomplished by means of novel glycosylated insulins having one of the general formulae:

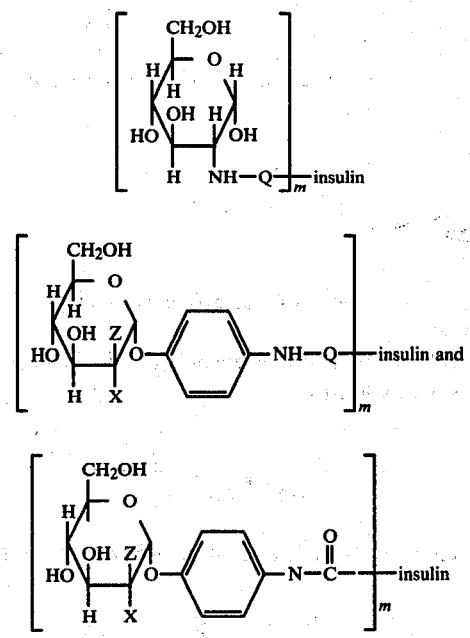

where m is an integer of 1 to 3, X and Z are different and are selected from the group consisting of —H and —OH and —Q— is a dicarboxylic acid spacer group having the formula:

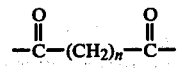

where n is an integer of from 2 to 6 and is preferably 2 or 3.

DETAILED DESCRIPTION OF THE INVENTION

Figure 1:
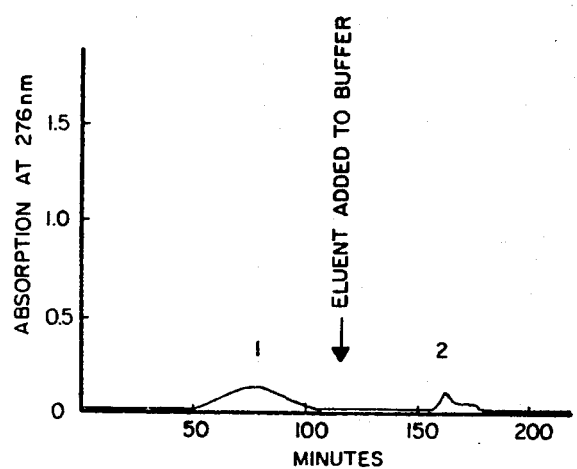

It is known that insulin can be combined with maltose as taught by Brownlee et al, in *Science*, 206, 223 (1979). However, this derivative of a disaccharide and insulin has been found not to possess any significant bioactivity in depressing blood sugar levels.

In the present invention, the intermediates prepared for coupling with insulin all consist of a glucose or mannose monosaccharide coupled to a spacer group. The spacer groups are derived from dicarboxylic acids, acid anhydrides or phenyl amines or a combinations thereof. The intermediates have the following general formula:

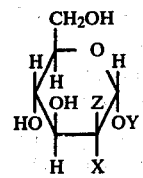

wherein
Y is a member selected from the group consisting of H,

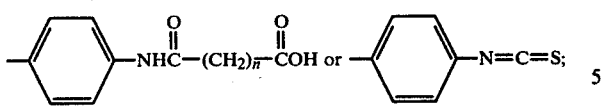

X is a member selected from the group consisting of —H, —OH or

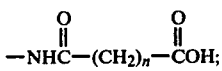

and

Z is a member of the group consisting of —H or —OH, with the proviso that when Y is —H, Z must also be —H and X must be

when X is —OH, Z must be —H and Y must be

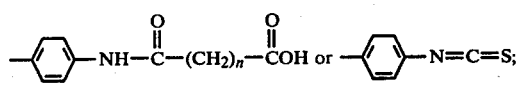

and when Z is —OH, X must be —H and Y must be

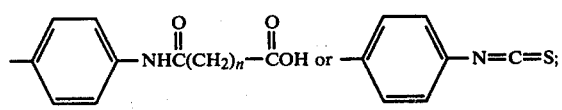

and where n is an integer of 2 to 6.

Preferably n is an integer of 2 or 3 and the

portion of the spacer is derived from succinic or glutaric anhydride.

The intermediates described by the above formula may be broken down into two subgroups.

The first subgroup is the glucosamine derivatives wherein Z is —H, Y is —H and X is

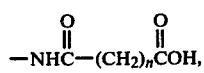

wherein n is an integer of 2 to 6

The second subgroup is the N-succinyl or N-glutarylamido-phenyl-α-D-gluco- and mannopyranosides and the p-isothiocyanotophenyl-α-D-gluco- and mannopyranosides wherein X and Z are different and are selected from the group consisting of —H and —OH and Y is a member selected from the group consisting of

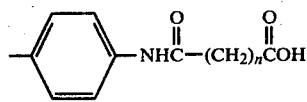

and

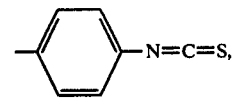

and n is an integer of 2 to 6.

The starting materials for the preparation of the sugar plus spacer glycocylated intermediates are glucosamine and p-nitrophenyl-α-D-gluco- and mannopyranosides and are commercially available.

The glucosamine may be reacted directly with an acid anhydride. Since the preferred spacers are succinyl and glutaryl moieties, the remainder of the discussion will be directed toward these derivatives. However, by appropriate synthesis, the corresponding derivatives from adipic, pimelic and suberic acids may also be utilized.

The p-nitrophenyl-α-D-gluco- and mannopyranosides are first treated to reduce the nitro group to an amino group. They may then be reacted with succinic and glutaric anhydrides to produce the corresponding N-succinyl- and N-glutaryl derivatives.

The p-aminophenyl-α-D-gluco- and mannopyranosides may also be reacted with thiophosgene to form the corresponding p-isothiocyanotophenyl-α-D-gluco- and mannopyranosides. The synthesis of these products are detailed in the examples which follow.

The glycosylated intermediates which follow are representative of the novel pyranosides which may be used to couple with insulin.

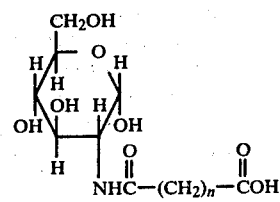

n = 2 N—succinyl glucosamine mp 174–175° C.
n = 3 N—glutaryl glycosamine mp 195–196° C.

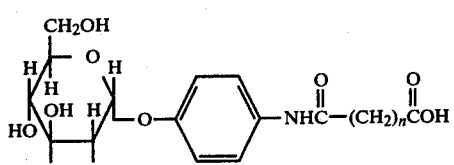

n = 2 p-(succinylamido)-phenyl-α-D-glucopyranoside mp 178–180° C.
n = 3 p-(glutarylmido)-phenyl-α-D-glucopyranoside mp 167–168° C.

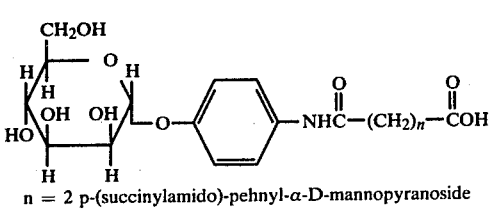

n = 2 p-(succinylamido)-pehnyl-α-D-mannopyranoside

-continued
mp 65–66° C.
n = 3 p-(glutarylamido)-phenyl-α-D-mannopyranoside
mp 134–136° C.

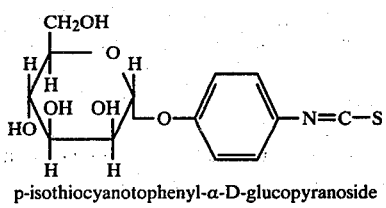

p-isothiocyanotophenyl-α-D-glucopyranoside

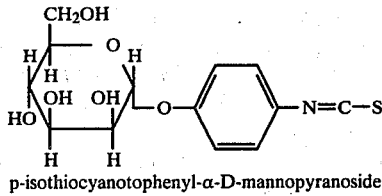

p-isothiocyanotophenyl-α-D-mannopyranoside

The structure of the insulin molecule is well known. It consists of two polypeptide chains A and B linked together by disulfide bonds of cystine. The N terminal group of the A fraction is glycine (Gly A-1) and the N-terminal group of the B fraction is phenylalanine (Phe B-1). Both N-terminal positions contain reactive free α-amino groups. Adjacent the C-terminal group of the B fraction is lysine having a free ε-amino group. It is believed that these free amino groups contribute to the problem of aggregation of insulin molecules with their eventual precipitation.

By blocking these groups with the above glycosylated intermediates, it was believed that the bioactivity of the insulin would not be greatly affected and that aggregation could be significantly inhibited or prevented. In addition, it is believed that glycosylated insulins may have other properties which may contribute to a chemical-sustained release mechanism for delivery of insulin to a diabetic in direct response to a change in blood sugar levels without the need for external or implanted sensing devices.

The reaction of the intermediates shown above was carried out by conversion of the carboxylic acid at the end of the spacer to a mixed anhydride through reaction with an alkylchloroformate and reaction of the mixed anhydride with the native insulin. The mixed anhydride reacts with one or more of the A-1, B-1 or B-29 free amino groups on the insulin to form a mono-, di- or triglycosylated insulin via an amide linkage The degree of substitution will depend on the molar ratio of intermediate to insulin and on reaction condition including pH. Generally, the molar ratio of intermediate to insulin will vary from 2 to 10. For purposes of reaction, a pH range of about 8 to 9.5 is preferable.

Because of the complexity of the reaction, one will seldom produce the glycosylated insulin as a mono-, di- or trisubstituted derivative. Rather, a mixture will be obtained as shown in the following examples.

For purposes of description, the glycosylated insulins may be divided into three categories.

The first category is those insulins prepared from glucosamines having a

spacer and possessing the general formula

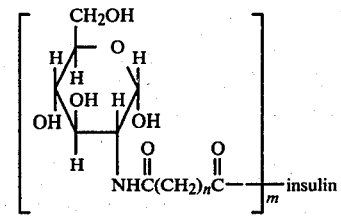

wherein n is an integer of 2 to 6, m is an integer of 1 to 3 and wherein the glycosyl group is attached to the insulin through one or more of the α-amino groups of the A-1 glycine, B-phenylalanine or ε-amino group of the B-29 lysine moieties of the insulin molecule.

Representative insulins are (glucosamidosuccinyl-)$_m$ insulin and (glucosamidoglutaryl-)$_m$ insulin.

A second category encompasses the gluco- and mannopyrano-sides coupled with a

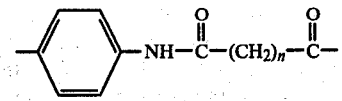

spacer having the general formula

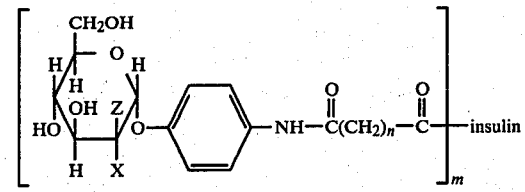

wherein X and Z are different and are selected from the group consisting of —H and —OH, n is an integer of 2 to 6 and m is an integer of 1 to 3, and wherein each glycosyl group is attached to the insulin by an amide linkage through one or more of the α-amino groups of the A-1 glycine, B-1 phenylalanine or ε-amino group of the B-29 lysine moieties of the insulin molecule.

Representative compounds include [p-(α-D-glucopyranosyloxy)-phenyl-N-succinamyl] insulin; [p-(α-D-glucopyranosyloxy)-phenyl-N-glutaramyl]$_m$ insulin; [p-(α-D-mannopyranosyloxy)-phenyl-N-succinamyl]$_m$ insulin; and [p(α-D-mannopyranosyloxy)-phenyl-N-glutaramyl]$_m$ insulin.

The third category is inclusive of gluco- and mannopyrano-sides coupled with a

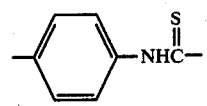

spacer having the general formula

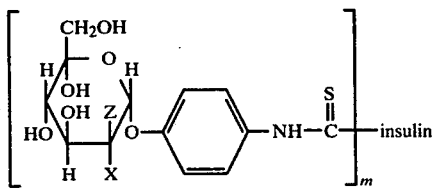

wherein Z and X are different and are selected from the group consisting of —H and —OH, and m is an integer of 1 to 3 and wherein each glycosyl group is attached to the insulin by a thioamide linkage through one or more of the α-amino groups of the A-1 glycine, B-1 phenylalanine or ε-amino group of the B-29 lysine moieties of the insulin molecule.

Representative compounds include [p-(α-D-glucopyranosyloxy)-phenyl-thiocarbamoyl-]$_m$ insulin and [p-(α-D-mannopyranosyloxy)-phenyl-thiocarbamoyl-]$_m$ insulin.

The glycosylated insulins prepared according to this invention may be administered to a diabetic in any conventional manner, i.e., subcutaneous, intramuscular or intraperitoneal injection. The dosage may be the same in terms of IU (international units) as will free or native insulin. Since dosages vary widely according to the needs of the patient, no attempt will be made to try to define dosage ranges. That will be left to the judgment of the patient's physician. Generally, dosages of 2 mg of insulin per day are required for a 60 kg. man.

The following examples show the preparation of the intermediate compounds, the preparation of glycosylated insulins, their bioactivity and ability to inhibit or prevent aggregation.

EXAMPLE I

Preparation of N-succinyl glucosamine

Glucosamine hydrochloride (0.05 m. 10.78 g) was dissolved in 15 mls of double distilled water and 0.05 m triethylamine (6.95 ml). To this was added, with stirring, succinic anhydride (0.05 m, 5.705 g) in 37.5 ml of acetone. The resulting mixture separated into two phases and sufficient water was added to bring both phases into a single solution. The solution was held at room temperature for four (4) hours for the reaction to be completed after which it was placed in a vacuum chamber and evaporated until a viscous, yellowish concentrated solution was obtained. The concentrate was measured and diluted with a triple amount of glacial acetic acid resulting in the formation of a white precipitate of N-succinyl glucosamine. The product was separated from the acetic acid solution by filtration and washed with ethanol and then petroleum ether. The yield of the resulting product was 39%. The product had a melting point of 174°–175° C. and a molecular weight within 2.5% of the calculated mole weight of 279.26. The structure and molecular weight were confirmed by IR, NMR and MS/GC spectra.

EXAMPLE II

Preparation of N-glutaryl glucosamine

The procedure of Example I was followed using glutaric anhydride. The product yield was 41%. The melting point was 195°–196° C. The calculated mole weight was 293.27. Structure was confirmed by IR and NMR spectra.

EXAMPLE III

Preparation of p-(succinylamido)-phenyl-α-D-glucopyranoside

In a first step, p-nitrophenyl-α-D glucopyranoside (14 m mole, 4.214 g) in 350 ml of methanol was reduced by mixing with ammonium formate (56 m mole, 3.54 g) and palladium on carbon particles at 25° C. The system was flushed for four (4) hours with nitrogen after which it was filtered and the filtrate was evaporated at a reduced pressure. The crude p-aminophenyl-α-D-glucopyranoside was purified by recrystallization in an ethanol-water (50:1) mixture. The yield was 71%. Its melting point was 169°–170° C. Structure and molecular weight were confirmed by IR and MS/GC spectra. The observed molecular weight was within 2.7% of the calculated mole weight of 271.27.

Following the procedure of Example I, p-aminophenyl-α-D-glucopyranoside was reacted with succinic anhydride to produce p-(succinylamido)-phenyl-α-D glucopyranoside in a yield of 53%. The melting point of the product was 178°–180°. Structure and molecular weight were confirmed by IR, NMR and MS/GC spectra. The observed molecular weight was within 2% of the calculated mole weight of 371.34.

EXAMPLE IV

Preparation of p-(glutarylamido)-phenyl-α-D-glucopyranoside

The procedure of Example III was followed using glutaric anhydride in the place of succinic anhydride. The p-(glutarylamido)-phenyl-α-D glucopyranoside was produced in a yield of 63% and had a melting point of 167°–168° C. Structure was confirmed by IR spectra and the calculated mole weight was 385.37.

EXAMPLE V

Preparation of p-(succinylamido)-phenyl-α-D-mannopyranoside

First, p-nitrophenyl-α-D-mannopyranoside was reduced to p-aminophenyl-α-D-mannopyranoside using the procedure outlined in Example III. The product yield was 91% and the product melted at 150°–153° C. The structure was verified by IR spectra.

The p-aminophenyl-α-D-mannopyranoside thus produced was reacted with succinic anhydride in the manner described in Example III to produce p-(succinylamido)-phenyl-α-D-mannopyranoside having a melting point of 65°–66° C. in 67% yield. Structure and molecular weight were confirmed by IR, NMR and MS/GC spectra. The observed molecular weight was within 2% of the calculated molecular weight of 371.34.

EXAMPLE VI

Preparation of p-(glutarylamido)-phenyl-α-D-mannopyranoside

The procedure outlined in Example V was followed substituting glutaric anhydride for succinic anhydride. The resulting p-(glutarylamido)-phenyl-α-D-mannopyranoside melting at 134°–136° C. was produced in a yield of 75%. The calculated molecular weight was 385.7. Structure was confirmed by IR spectra.

EXAMPLE VII

Preparation of p-isothiocyanotophenyl-α-D-glucopyranoside

To a solution of p-(aminophenyl)-α-D-glucopyranoside in 80% aqueous ethanol was added a molar excess of thiophosgene (CSCl$_2$). The reaction was carried out at room temperature and was complete in a manner of minutes. A crystalline product was obtained. The calculated mole weight was 313.3.

EXAMPLE VIII

Preparation of p-isothiocyanotophenyl-α-D-mannopyranoside

The procedure of Example VII may be followed substituting p-(aminophenyl)-α-D-mannopyranoside for the corresponding glucopyranoside to produce p-isothiocyanato-phenyl-α-D-mannopyranoside.

In confirming the synthesis of the above combinations of glucosamine or p-aminophenyl-α-D gluco- and mannopyranosides with succinic and glutaric anhydrides, the following tests were utilized. An infrared spectrophometer (Beckman Microlab 620 MX Computing Infrared Spectrophometer) was utilized to determine the reaction between the amino group and the anhydride by detecting the presence of an amide bond. Samples were prepared as 0.5% (w/w) KB$_r$ pellets. The presence of the amino group prior to reaction was detected by the N—N bending vibration at 1650–1580 cm$^{-1}$. The p-aminophenyl derivatives prepared by the reduction of the corresponding p-nitrophenyl derivatives did not show N—O stretching bands at 1580 cm$^{-1}$ and 1330 cm$^{-1}$ indicating that the reduction reaction was complete. The formation of the amide bond was shown by the presence of a C=O stretching band at 1660 cm$^{-1}$ and a N—H bending mode at 1600 cm$^{-1}$. A normal dimeric carboxylic C=O stretching band was also found at about 1725 cm$^{-1}$. These data confirm a distinct amide band indicating the completion of the coupling reaction between the amino and dicarboxylic acid anhydride reactants.

The molecular weights were determined by MS/GC spectra using a LKB 9000S MS/GC spectrophometer interfaced with a DEC PDP 11/34 computer. The volatility of the carbohydrate derivatives was enhanced by using trimethylsilyl derivatization of the hydroxyl and carboxylic acid groups. In all instances, the observed molecular weight of the trimethylsilyl derivatives was within 2.5±0.5% of the calculated theoretical values.

The presence of the

moiety was confirmed by proton MNR spectra using a JOEL JNM-FX 270 Fourier Transform NMR spectrophotometer. The samples were dissolved in D$_2$O and sodium 2,2-dimethyl-2-silapentane-5-sulfonate (DSS) was used as an internal reference. For example, in the p-(succinylamido-α-D-glucopyranoside, the proton signals of the methylene groups in the succinyl moiety was observed at δ=2.71 as a triplet. The peak area was proportional to the number of protons representing the four methylene protons of the succinyl moiety.

The melting points were determined by the capillary melting point method.

The yield of the above glucose and mannose derivatives with the dicarborylic acid anhydrides varied between about 39 and 91%. The variation in yield is thought to be due to the use of a limited solvent (ethanol-water mixture) for recrystallization. The yield should increase with the selection of a proper solvent for the recrystallization procedure.

The recoupling action of the above described glycosylamidocarboxylic acid derivatives with insulin is carried out via a mixed anhydride method wherein the mixed anhydride is not isolated from the reaction mixture. The glycosylamidocarboxylic acid is converted to mixed anhydride by reaction with isobutylchloroformate and the resulting mixed anhydride is reacted with a free amino group from the insulin molecule to form an amide linkage. The procedure is described in general by Erlanger et al in *J. Biol. Chem.*, 228,713 (1957) and Arekatsu et al in *J. Immunal.*, 97, 858 (1966).

There are three primary sites available on the insulin molecule for reaction with the glycosylamido-carboxylic acid derivatives and the insulin may be coupled with one, two or three of these derivatives. These available sites include the α-amino groups of the glycine (Gly A-1), and phenylalanine (Phen B-1) and the ε-amino group of the lysine (Lys B-29) portions of the insulin molecule. The pKapp values of these groups are: 8.0 for Gly A-1, 6.7 for Phen B-1 and 11.2 for Lys B-29.

Because insulin becomes denatured at too high a pH and to maintain the ε-amino group of the Lys B-29 moiety in a less reactive protonated state, the pH of the coupling reaction between the glycosyl-amido-carboxylic acids and insulin was chosen to be between 7.5 and 10 and preferably at 9.5. Therefore, the α-amino groups of the Gly A-1 and Phe B-1 positions are thought to be the primary reaction sites. However, trisubstituted glycosylated insulin may also be produced by the above method since a free ε-amino group from the Lys B-29 moiety could be formed by deprotonation through the use of the highly nucleophilic tri-N-butylamine added to complex the HCl produced during the anhydride formation by the isobutylchloroformate. Also, based on the Henderson-Hasselbach equation, at a pH of 9.5, about 2% of the ε-amino groups of Lsy B-29 exist in equilibrium in the free or deprotonated form. Therefore, a significant amount of trisubstituted glycosylated insulin may be prepared. However, because of the pH chosen, i.e., 9.5 and the more reactive free amino groups of Gly A-1 and Phen B-1 at that pH, the glycosylated insulin will be primarily a mixture of di and tri-substituted derivatives. Some monosubstitution may also be present.

In the following examples, the unreacted insulin is removed from the glycosylated insulin by means of affinity chromatography using a column containing Sepharose beads bound with Con-A (Concanavalin-A).

It is known that Con-A has a binding affinity for saccharides. Therefore, the more glycosyl moieties coupled to the insulin, the greater that glycosylated insulin will be bound to the Con-A in the chromatography column. One would then expect the unreacted insulin to be eluted through the column first followed by mono-, di- and tri-glycosylated insulins in that order.

This is generally true. However, some glycosylated derivatives may be eluted from the column along with unreacted insulin.

The following example is typical of the process of separating unreacted insulin from glycosylated insulin by affinity chromatography with Con-A.

EXAMPLE IX

Preparation of N-succinylglucosamine Coupled Insulin (Glucosamidossinyl Insulin)

Bovine insulin (87.77 μmoles 500 mg) was dissolved in 200 mls of an equal volume mixture of distilled water and dimethylformamide (DMF) and adjusted to a pH of 9.5 with 0.1N sodium hydroxide and was then cooled in an ice bath. N-succinylglucosamine, (800 μmoles) was dissolved in a solution of DMF containing 800 μmoles each of tri-N-butylamine and isobutylchloroformate and kept at 0° C. for 20 minutes. An additional 1.6 m mole of tri-N-butylamine was added to this solution which was then mixed, with stirring, to the insulin solution. The reaction mixture thus formed was pH adjusted to 9.5 with 0.1N sodium hydroxide and kept for one hour at 0° C. The mixture was then kept at room temperature overnight and then dialyzed through a semipermeable membrane for two days against distilled water to remove unreacted N-succinylglucosamine. The distilled water was maintained at 4° C. and was changed every four hours.

The glycosylated insulin remaining inside the dialysis membrane was lyophilized and dissolved in the tris-buffer solution described below. The resulting solution was sterilized by filtration to remove any bacteria present.

The sterilized product was placed on a 2.5×60 cm column containing beads of commercial Con A (Concanavalin-A)-bound To Sepharose 4B (Sigma Chemical Co., St. Louis, Mo.). The unreacted insulin was removed from the column using a 0.02 m tris-buffer eluent also containing 1 mm $MnCl_2$, 1 mm $CaCl_2$ and 0.5 m NaCl. The eluent had a pH of 7.4 and was maintained at 4° C. The flow rate was maintained at 72 ml/hr and 7.0 ml fractions were collected and analyzed by UV spectra at A 276 nm for the presence of insulin. A colorimetric determination for sugars at 480 nm using a phenol-sulfuric test also showed the presence of some N-succinyl-glucosamine coupled insulin.

After approximately 105 minutes as shown by FIG. 1, all of the unreacted insulin (component 1) had been collected as monitored by the UV spectra at 276 nm. At that time, 0.1 m α-methyl-D-mannopyranoside was added to the tris-buffer solution as an eluent and the flow rate was maintained at 72 ml/hr. After approximately 200 minutes, all of component 2, consisting of N-succinylglucosamine, coupled insulin, had been collected as also shown in FIG. 1.

The low intrinsic binding capacity of the glucosamine moiety to Con-A was thought to be responsible for the mixed elution of free insulin and glycosylated insulin in component 1. Due to the low absorptivity of the glycosylated insulin in Component 2 at 480 nm, the degree of substitution could not be determined.

The glycosylated insulin in component 2 was lyophilized for determination of its ability to depress blood sugar levels.

The corresponding N-glutarylglucosamine coupled insulin (glucosamidoglutaryl insulin) was prepared in a similar manner.

EXAMPLE X

Preparation of p-(succinylamido)-phenyl-α-D-glucopyranoside Coupled Insulin

[p-(α-D-glucopyranosyloxy)-phenyl-N-succinamyl insulin]

Figure 2:
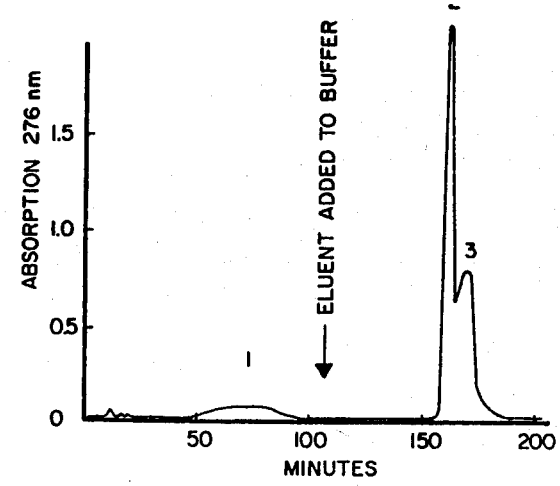

The procedure of Example IX was followed for reacting the p-(succinylamido)-phenyl-α-D-glucopyranoside from Example III with bovine insulin. The results are shown in FIG. 2. Component 1 in FIG. 2 consisted of free insulin and some glycosylated insulin as verified by the phenol-sulfuric acid method at 480 nm. Components 2 and 3 were collected and tested by the phenol-sulfuric acid method for the presence of the glycosyl radical as well as at 276 nm for insulin. Due to the large amount of eluent required to separate component 3, it can be predicted that Component 3 contained more glycosyl radicals on the insulin than Component 2. The area under the curves of Components 2 and 3 was 58.9% and 41.1% respectively. Component 2 was primarily diglycosyl substituted insulin and Component 3 was primarily the triglycosyl substituted derivative. Therefore, $0.589 \times 2 + 0.411 \times 3 = 2.411$ which would be the average number of glycosyl derivatives on the insulin contained in Components 2 and 3 combined. This degree of substitution was consistent with the phenol-sulfuric acid test which showed 2.3 glycosyl groups per insulin molecule. The phenol-sulfuric acid test is detailed by Dubois et al, *Analytical Chemistry*, 28, 350 (1956).

After collection Components 2 and 3 were combined and dialyzed to remove the eluent, α-methyl-D-mannopyranoside, the purified product was lyophilized for biological testing.

Following the same procedure, the corresponding p-(glutarylamido)-phenyl-α-D-glucopyranoside coupled insulin [p-α-D-glucopyranosyloxy)-phenyl-N-glutaramyl insulin] was prepared.

EXAMPLE XI

Preparation of p-(succinylamido)-phenyl-α-D-mannopyranoside Coupled Insulin

[p-(α-D-mannopyranosyloxy)-phenyl-N-succinamyl insulin]

Figure 3:
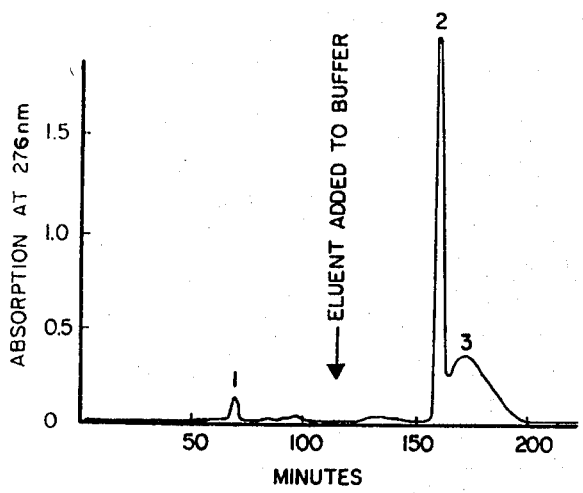

The procedure outlined in Example X was followed and the elution profile is shown in FIG. 3. Component 1 was unreacted free insulin since the phenol-sulfuric acid test was negative. The average degree of glycosyl radicals attached to insulin for the combination of components 2 and 3 was 2.5 according to the phenol-sulfuric acid test. The area under the curves for components 2 and 3 was 34% and 66% respectively indicating an average degree of substitution of 2.66 which compares closely with the above test results.

The purified lyophilized product was retained for testing for blood sugar reduction.

The corresponding p-(glutarylamido)-phenyl-α-D-mannopyranoside coupled insulin [p-(α-D-mannopyranosyloxy)-phenyl-N-glutaramyl insulin] was prepared and purified by the above procedures.

EXAMPLE XII

Figure 4:
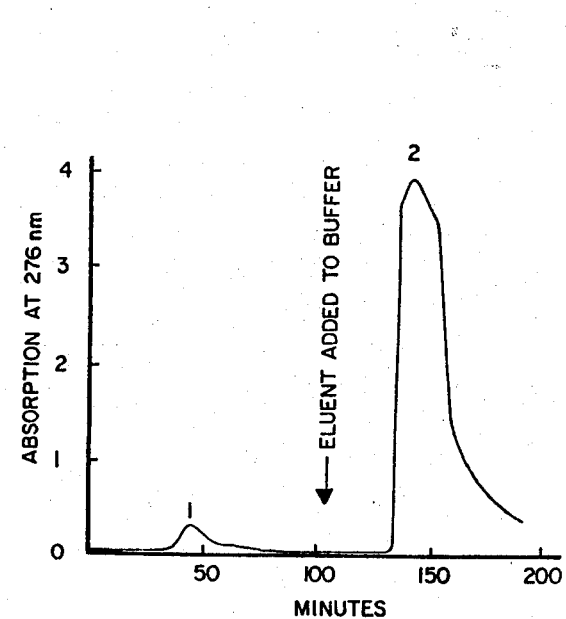

Preparation of p-(α-D-glucopyranosyloxy)phenyl-thiocarbamoyl Insulin p-(Isothiocyanotophenyl)-α-D-glucopyranoside (355.08 μmoles) from Example VII was dissolved in a solution of three parts pyridine and one part water at 5° C. and the pH was adjusted to 8.0 with 0.1N NaOH. Bovine insulin (177.54 μmoles, 1 gm) was prepared using a pyridine-water solvent and combined with the glucopyranoside solution. The combined solutions were maintained at 5° C. at a pH of 8.0 for one hour and then allowed to stand overnight at room temperature. The reaction product consisting of p-(α-D-glucopyranosyloxy)-phenyl-thiocarbamoyl insulin was then dialyzed as in Example IX to remove unreacted p-(isothiocyanotophenyl)-α-D-glucopyranoside and the remaining product was lyophilized, dissolved in tris-buffer and subjected to affinity chromatography on a Con-A Sephorase 4B column as in Example IX. The flow rate was 26 ml/hr at 4° C. and 5.0 ml fractions were collected. The elution profile is shown in FIG. 4. Component 1 contained both free insulin and glycosylated insulin and Component 2 consisted of p-(α-D-glucopyranosyloxy)-phenyl-thiocarbamoyl insulin having an average of 1.5 glycosyl groups per insulin molecule.

The product from component 2 was dialyzed to remove the α-methyl-D-mannopyranoside eluent and was then lyophilized for biological testing.

EXAMPLE XIII

Aggregation Studies

One of the problems associated with free or native insulin is its tendency to aggregate and eventually crystallize out of solution, thereby reducing its bioavailability. With the glycosylated insulins this tendency is greatly reduced since portions of the active amino sites on the Gly A-1, Phe B-1 and Lys B-29 in insulin are blocked by the coupling reaction of glycosyl groups.

Bulk aggregation studies with free insulin compared with glycosylated insulins were carried out by two methods. In a bulk aggregation study, various aqueous insulin and glycosylated insulin solutions containing 0.1 mg/ml of insulin were stirred at 1555 rpm until aggregation was visually observed or up to two weeks. In a second test, solutions containing the same insulin concentration were deposited on polyurethane (Biomer) and microscopically observed for aggregation.

The results are as follows:

| | TIME REQUIRED FOR AGGREGATION | | | |
|---|---|---|---|---|
| Aggregation | | Glycosylated Insulins | | |
| Test | Free Insulin | A | B | C |
| Bulk | 2–3 days | 2 weeks | 2 weeks | 2 weeks |
| Polyurethane | 1–2 days | 2 weeks | 2 weeks | 8 days |

A = p(α-D-glucopyranosyloxy)-phenyl-N—succinamyl insulin
B = p(α-D-mannopyranosyloxy)-phenyl-N—succinamyl insulin
C = p(α-D-glucopyranosyloxy)-phenyl-thiocarbamoyl insulin It is obvious from the above results that the glycosylated insulins are much more stable against aggregation than free insulin and will thus have a better storage life.

EXAMPLE XIV

Bioactivity of Glycosylated Insulins

The bioactivity of the glycosated insulins described herein was determined by a blood sugar depression test and compared to commercial insulin preparations and controls. In this test, replicates of standard laboratory rats were fasted for twenty hours. After measuring baseline blood sugar levels, a 1 mg/kg dose of either free or glycosylated insulin was injected via an intraperitoneal route. The blood sugar level in each rat was measured colormetrically 20 minutes after the injection. The results are given in the following table:

| BLOOD SUGAR DEPRESSION (BSD) TEST | | |
|---|---|---|
| Type of Insulin | No. Rats | Blood Sugar Concentration after 20 min. IP. injection (± S.E.M.) mg/dl |
| SIGMA INS (21F-0375)25.5 IU/MG. | 5 | 32.66 ± 1.10 |
| LILLY INS (615-70N-80)100 IU/MG. | 5 | 31.87 ± 1.93 |
| Glucosamidosuccinyl insulin (unpurified) | 5 | 37.80 ± 1.13 |
| Glucosamidoglutaryl insulin (unpurified) | 4 | 45.92 ± 3.30 |
| p-(α-D-glucopyranosyloxy)-phenyl-N—succinamyl insulin | 5 | 40.87 ± 1.32 |
| p-(α-D-glucopyranosyloxy)-phenyl-N—glutaramyl insulin | 5 | 40.40 ± 2.53 |
| p-(α-D-mannopyranosyloxy)-phenyl-N—succinamyl insulin | 5 | 44.80 ± 2.37 |
| p-(α-D-mannopyranosyloxy)-phenyl-N—glutaramyl insulin | 5 | 40.60 ± 0.80 |
| p-(α-D-glucopyranosyloxy)-phenyl-Thiocarbamoyl insulin | 5 | 44.67 ± 2.21 |
| Control | *44 | 64.62 ± 0.61 |

*Includes all rats used in test at baseline level.

It is evident from the above that the seven glycosylated insulins prepared, as described herein, all possess significant biological activity in depressing blood sugar levels.

What is claimed is:

1. A method of depressing the blood sugar level in a diabetic patient which comprises administering to said patient, in a pharmaceutically acceptable carrier, an effective amount of a glycosylated insulin having the formula

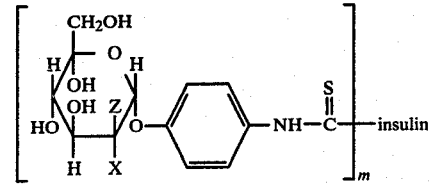

wherein Z and X are different and are selected from the group consisting of —H and —OH, and m is an integer of 1 to 3 and wherein each glycosyl group is attached to the insulin by a thioamide linkage through one or more of the α-amino groups of the A-1 glycine, B-1 phenylalanine or ε-amino group of the B-29 lysine moieties of the insulin molecule.

2. A method according to claim 1 wherein the effective amount of the glycosylated insulin has been determined based upon the needs of the patient.

3. A method according to claim 2 wherein Z is —H and X is —OH.

4. A method according to claim 2 wherein Z is —OH and X is —H.

* * * * *